(12) United States Patent
Kim

(10) Patent No.: US 6,249,699 B1
(45) Date of Patent: Jun. 19, 2001

(54) CARDIOVERTER AND METHOD FOR CARDIOVERTING AN ATRIAL TACHYARRHYTHMIA IN THE PRESENCE OF ATRIAL PACING

(75) Inventor: Jaeho Kim, Redmond, WA (US)

(73) Assignee: Cardiac Pacemakers, Inc., Minneapolis, MN (US)

( * ) Notice: Subject to any disclaimer, the term of this patent is extended or adjusted under 35 U.S.C. 154(b) by 0 days.

(21) Appl. No.: 09/148,094

(22) Filed: Sep. 3, 1998

(51) Int. Cl.[7] .............................. A61N 1/39; A61N 1/362
(52) U.S. Cl. .................................................... 607/4
(58) Field of Search ........................................ 607/4

(56) References Cited

U.S. PATENT DOCUMENTS

| | | | |
|---|---|---|---|
| Re. 36,765 | * 7/2000 | Mehra | 607/4 |
| 5,676,687 | * 10/1997 | Ayers | 607/4 |
| 5,766,224 | 6/1998 | Alferness et al. | |
| 5,814,079 | * 9/1998 | Kieval | 607/4 |
| 5,910,120 | * 6/1999 | Kim et al. | 600/509 |
| 6,128,529 | * 10/2000 | Esler | 607/4 |

OTHER PUBLICATIONS

Medtronic, Jewel AF Arrhythmia Management Device System Reference Guide, Feb., 1997.

* cited by examiner

Primary Examiner—Carl H. Layno
(74) Attorney, Agent, or Firm—Foley & Lardner

(57) ABSTRACT

An atrial cardioverter which includes a pacemaker for applying atrial pacing pulses to an atrium of a heart, an atrial tachyarrhythmia detector for detecting an atrial tachyarrhythmia of the heart, and an R wave detector for detecting R waves of the heart. A cardioverting stage including a timer for timing time spans between immediately successive R waves and atrial pacing pulses applies cardioverting electrical energy to the atria of the heart responsive to a time span exceeding a predetermined duration.

12 Claims, 2 Drawing Sheets

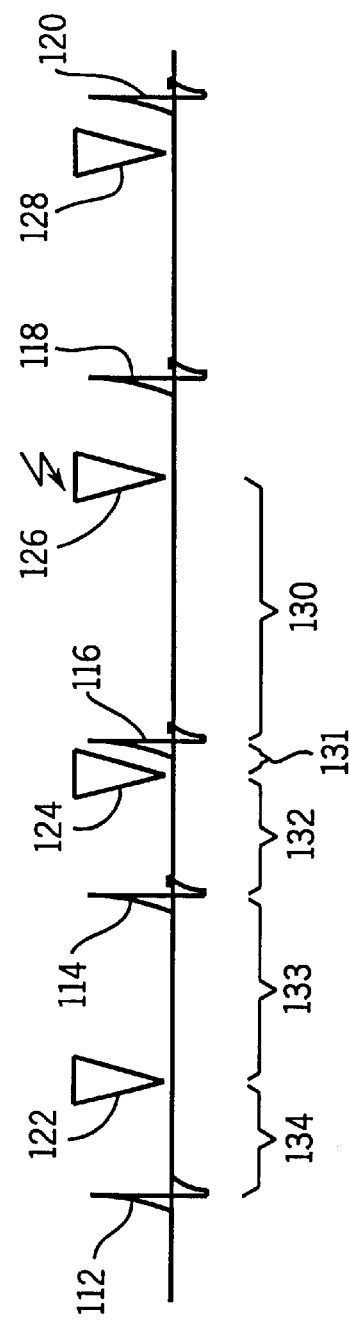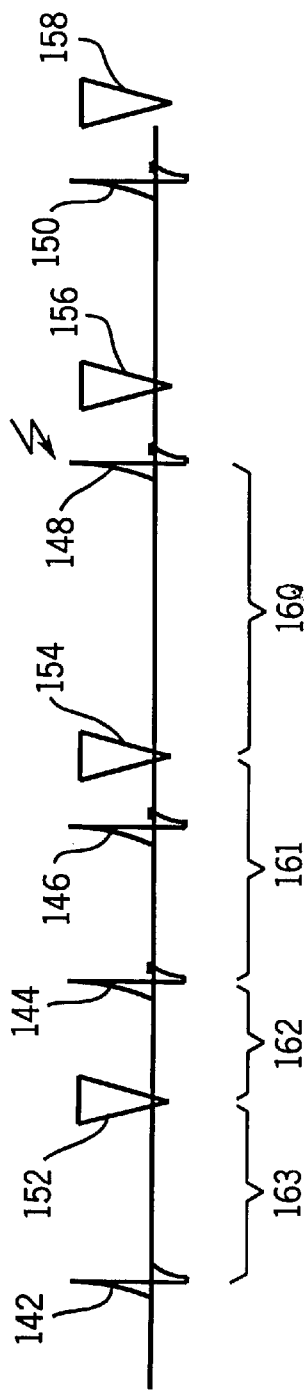

Page 1 / 2 …

CARDIOVERTER AND METHOD FOR CARDIOVERTING AN ATRIAL TACHYARRHYTHMIA IN THE PRESENCE OF ATRIAL PACING

BACKGROUND OF THE INVENTION

The present invention generally relates to a method and system for cardioverting an atrial tachyarrhythmia. The present invention is more particularly directed to such a system and method which is capable of safely cardioverting an atrial tachyarrhythmia in the presence of atrial pacing.

Atrial fibrillation is probably the most common cardiac arrhythmia. Although it is not usually a life-threatening tachyarrhythmia, it is associated with strokes thought to be caused by blood clots forming in areas of stagnant blood flow as a result of prolonged atrial fibrillation. In addition, patients afflicted with atrial fibrillation generally experience rapid and irregular beating of the heart and may even experience dizziness as a result of reduced cardiac output.

Atrial fibrillation occurs suddenly, and many times can only be corrected by discharging electrical energy into the atria of the heart of the patient. This treatment is preferably synchronized to a detected R wave of the heart in order to avoid shocking the atria during the T wave or vulnerable period of the heart. The amount of energy which may be required to successfully cardiovert the atria can be as low as one joule and as high as six joules. In most cases, energy of about two to four joules is required to cardiovert atrial fibrillation back to normal sinus rhythm (NSR).

Implantable atrial defibrillators are known which detect the presence of atrial fibrillation and provide a single cardioverting pulse of electrical energy to the atria when atrial fibrillation is detected. One such defibrillator disclosed in U.S. Pat. No. 5,207,219 applies the therapy in synchrony with a detected R wave and after a minimum cardiac cycle interval to avoid therapy application during the ventricular vulnerable period of the heart thereby preventing the induction of a lethal ventricular arrhythmia. This therapy has been found to be very effective and safe. It, however, assumes that no other therapy is being applied to the heart at the time that the defibrillator is detecting for a suitable R wave for synchronized therapy delivery.

Some patients, and particularly those with sick sinus syndrome, require continuous atrial pacing because of a dysfunctional Sinus node precluding the production of intrinsic atrial activations or P waves. For those patients, the right atrium is continuously paced at a minimum or rate responsive rate. The pacing is performed in an inhibit mode to inhibit an atrial pacing pulse should a P wave be spontaneously produced by the heart.

To accommodate or treat a patient with sick sinus syndrome who also has episodes of an atrial tachyarrhythmia, such as atrial fibrillation, an atrial cardioverter must be able to both continuously pace the atria and cardiovert the atria in the presence of such pacing. Unfortunately, during atrial fibrillation, the amplitude of atrial activity becomes drastically diminished and intrinsic atrial activity may be undersensed. This essentially reduces the atrial pacing to fixed rate, non-inhibited pacing, commonly referred to as AOO pacing.

As can be appreciated from the above, under these conditions, chaotic heart activity is evident. Not only are the atria being paced at a fixed rate, but R waves, at a rapid and irregular rate are also being produced by the heart. In order to find a safe and effective time to apply tachyarrhythmia therapy, measures not heretofore known must be used. The present invention provides such measures.

SUMMARY OF THE INVENTION

The invention provides an atrial cardioverter including a pacemaker for applying atrial pacing pulses to an atrium of a heart, an atrial tachyarrhythmia detector for detecting an atrial tachyarrhythmia of the heart, and an R wave detector for detecting R waves of the heart. The cardioverter further includes a cardioverting stage including a timer for timing time spans between immediately successive R waves and atrial pacing pulses for applying cardioverting electrical energy to the atria of the heart responsive to a time span exceeding a predetermined duration.

The invention further provides an atrial cardioverter for cardioverting atria of a heart in the presence of atrial pacing pulses being applied to the heart. The cardioverter includes means for determining when the atrial pacing pulses are applied to the heart, an atrial tachyarrhythmia detector for detecting an atrial tachyarrhythmia of the heart, and an R wave detector for detecting R waves of the heart. The cardioverter further includes a cardioverting stage including a timer for timing time spans between immediately successive R waves and atrial pacing pulses for applying cardioverting electrical energy to the atria of the heart responsive to a time span exceeding a predetermined duration.

The invention still further provides a method of cardioverting atria of a heart in the presence of applied pacing pulses to the atria of a heart. The method includes the steps of determining when the atrial pacing pulses are applied to the heart, detecting an atrial tachyarrhythmia of he heart, and detecting R waves of the heart. The method further includes timing time spans between immediately successive R waves and atrial pacing pulses, and applying cardioverting electrical energy to the atria of the heart responsive to a time span exceeding a predetermined duration.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein;

FIG. 2 is an electrogram illustrating the operation of the present invention in accordance with a preferred embodiment thereof; and FIG. 3 is another electrogram illustrating the operation of the present invention in accordance with another embodiment thereof.

DETAILED DESCRIPTION OF THE PREFERRED EMBODIMENT

Figure 1:
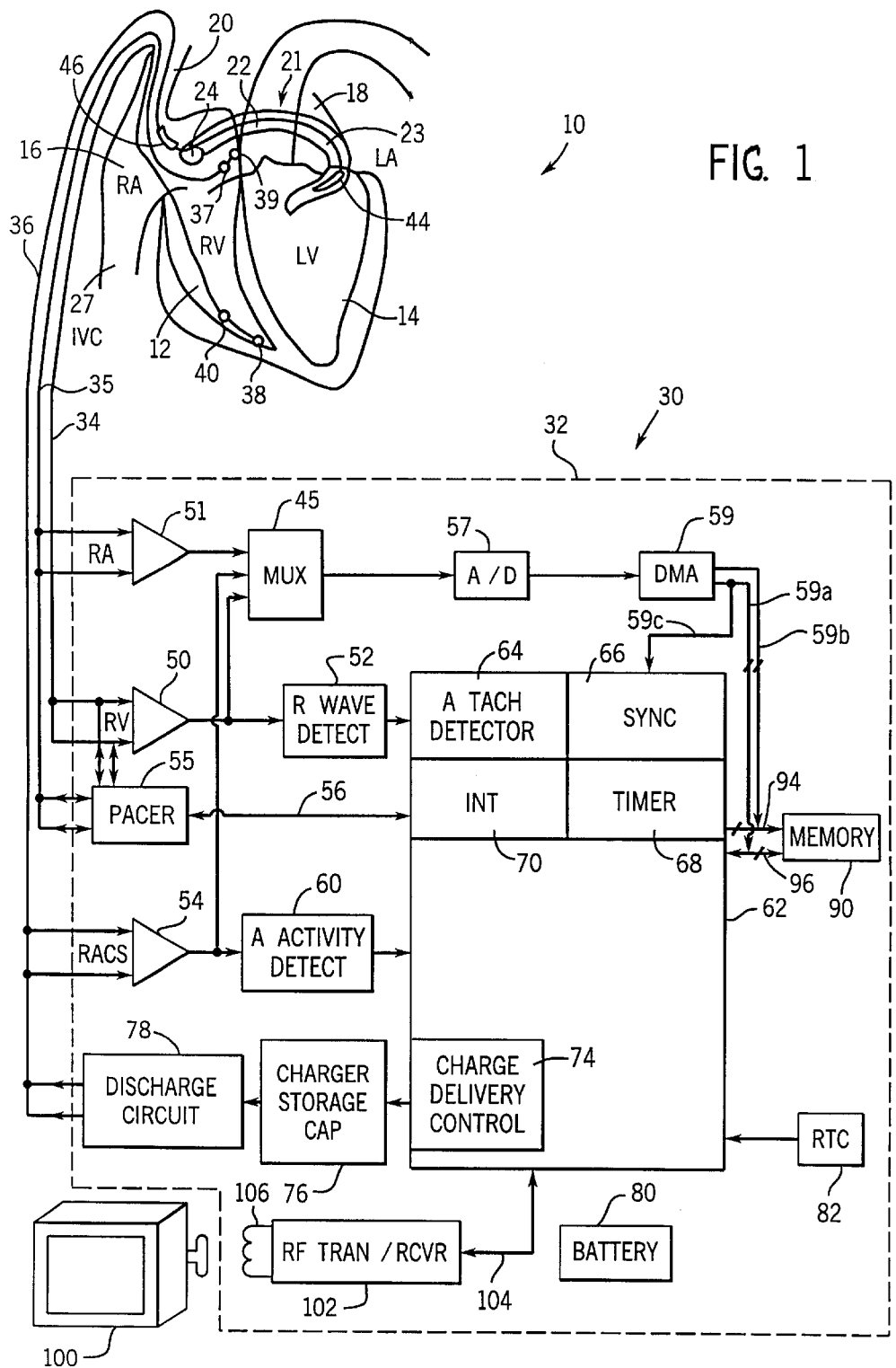
FIG. 1 is a schematic block diagram of a fully implantable atrial cardioverter/defibrillator embodying the present invention.

Prior to referring to FIG. 1, a general description of a typical or normal cardiac cycle may be helpful in understanding the operation and various aspects of the present invention. The beginning of a cardiac cycle in normal sinus rhythm is initiated by a P wave which is normally a small positive wave. The P wave induces depolarization of the atria of the heart. Following the P wave there is a cardiac cycle portion which is substantially constant having a time duration on the order of, for example, 120 milliseconds.

The QRS complex of the cardiac cycle then normally occurs after the substantially constant portion. The dominating feature of the QRS complex is the P wave which is a rapid positive or negative deflection. The R wave generally has an amplitude greater than any other wave of the cardiac cycle and is characterized by a rapid deviation from and return toward baseline. The R wave is the depolarization of the ventricles. The QRS complex is completed by the S wave which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds.

Referring now to FIG. 1, it illustrates a fully implantable atrial cardioverter/defibrillator 30 embodying the present invention shown in association with a schematically illustrated human heart 10. The portions of the heart 10 illustrated in the sole figure are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 27.

The atrial defibrillator 30 generally includes an enclosure 32 for hermetically sealing the internal circuit elements of the atrial defibrillator to be described hereinafter, a ventricular endocardial or first lead 34, a right atrial endocardial or second lead 35 and an intravascular or third lead 36. The enclosure 32 and leads 34, 35, and 36 are arranged to be implanted beneath the skin of a patient so as to render the atrial defibrillator 30 fully implantable.

The intravascular lead 36 generally includes a first or tip electrode 44 and a second proximal electrode 46. As illustrated, the lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 are further used to deliver defibrillating electrical energy to the atria. The electrodes 44 and 46 are preferably elongated cardioverting electrodes.

The first lead 34 preferably comprises a ventricular endocardial lead having bi-polar pair electrodes 38 and 40 arranged for establishing electrical contact with the right ventricle 12 of the heart 10. The electrodes 38 and 40 permit bi-polar sensing of ventricular activations in the right ventricle and pacing in the right ventricle. As illustrated, the lead 34 is fed through the superior vena cava 20, into the right atrium 16, and then into the right ventricle 12.

The second lead 35 preferably comprises a right atrial endocardial lead having bi-polar pair electrodes 37 and 39. Electrode 39 preferably is a helical screw-in coil for both providing fixation of the lead 35, as known in the art, and establishing electrical contact with the right atrium 16 of the heart 10. The electrodes 37 and 39 permit localized bipolar sensing of heart activity in the right atrium and pacing, including fixed or rate responsive pacing, in the right atrium. As illustrated, the lead 35 is fed through the superior vena cava 20 and into the right atrium 16.

Within the enclosure 32, the atrial defibrillator 30 includes a first sense amplifier 50, a second sense amplifier 51, and a third sense amplifier 54 and an R wave detector 52. The first sense amplifier 50 forms an RV channel which provides an electrogram of the sensed right ventricular heart activity at an input of multiplexer 45 and to an input of an R wave detector 52. The second sense amplifier 51 forms an RA channel to provide an electrogram of the sensed right atrial heart activity at its output which is coupled to another input of multiplexer 45. The third sense amplifier 54 forms an RACS channel to provide an electrogram of the sensed right atrium to left atrium heart activity at its output which is coupled to another input of the multiplexer 45 and an atrial activity detector 60. The sense amplifiers may include a differentiating filter so that the electrograms which they provide are differentiated electrogram signals.

The R wave detector 52 provides one or more output pulses for each R wave sensed during a cardiac cycle of the heart. To that end, the R wave detector may include a further differentiating filter for differentiating the differentiated cardiac signal provided by sense amplifier 50 resulting in a twice differentiated second cardiac signal. The R wave detector 52 may further include a threshold circuit for setting an upper and lower threshold which provides an output when the twice differentiated second cardiac signal transitions beyond either the upper or lower thresholds.

Finally, the R wave detector preferably further includes an output pulse rate limiter (not shown) having a programmable pulse repetition time interval. The pulse repetition time interval is set to be as short as possible to allow detection of the last threshold crossing for an R wave. The R wave detector 52 thus provides at least one such pulse to indicate the beginning of each detected R wave and one such pulse to indicate the completion of each detected R wave so that the beginning and end of each R wave may be determined.

The atrial activity detector 60 also preferably includes a similar further differentiating filter (not shown) and output pulse rate limiter (not shown). This similarly enables the atrial activity detector 60 to provide at least one output pulse to indicate the beginning of each sensed P-wave and another to indicate the end of each sensed P wave.

The enclosure 32 of the atrial defibrillator 30 further includes a microprocessor 62. The microprocessor 62 is preferably implemented in accordance with this embodiment of the present invention to result in a plurality of functional stages. The stages include an atrial tachyarrhythmia detector, preferably in the form of an atrial fibrillation detector 64, a synchronization stage 66, a timer 68, an interrupt stage 70, and a charge delivery and energy control stage 74.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, in the memory at the addresses defined by multiple-bit addresses conveyed over the address bus 94 and conveys the operating parameters and data to the memory 90 over the multiple-bit data bus 96. During a read operation, the microprocessor 62 obtains data or operating parameters from the memory at the storage locations identified by the multiple-bit addresses provided over the address bus 94 and receives the operating parameters and data from the memory over the bi-directional data bus 96.

For entering operating parameters into the memory 90, the microprocessor 62 receives the programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or receives programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from the external controller 100 and for transmitting data to the external controller 100. One preferred communication system is disclosed in U.S. Pat. No. 5,342,408 which issued on Aug. 30, 1994 for "Telemetry System for an Implantable Cardiac Device," which patent is assigned to the assignee of the present invention and incorporated herein by reference.

The atrial defibrillator 30 further includes an analog to digital converter 57 and a direct memory access controller (DMA) 59. The analog to digital converter 57 has an input coupled to the output of the multiplexer 45 for receiving the electrogram signals generated by the sense amplifiers 50, 51, and 54. During a data acquisition, the analog to digital converter 57 converts the electrogram signals into digital data. The digital data is received by the DMA 59 which conveys the digital data to memory 90 over a data bus 59a for storage in memory at predetermined locations selected by the DMA 59 over an address bus 59b. The electrogram signals thus stored in digital form representing activity of the heart are thereafter utilized by the microprocessor to perform various functions. For example, for atrial fibrillation detection, the atrial fibrillation detector 70 preferably utilizes the stored data from the RACS channel for detecting the presence of atrial fibrillation of the heart.

The atrial defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. The defibrillator 30 further includes a depletable power source 80, such as a lithium battery, for providing power to the electrical components of the atrial defibrillator 30, and a real time clock 82.

The atrial defibrillator 30 lastly includes a pacer 55 which is coupled to electrodes 38 and 40 of lead 34 and to electrodes 37 and 39 of lead 35. The pacer 55 preferably includes circuitry for sensing ventricular activity with electrodes 38 and 40 and pacing circuitry for applying pacing pulses to the ventricles with electrodes 38 and 40. Similarly, the pacer 55 preferably includes circuitry for sensing atrial activity with electrodes 37 and 39 and pacing circuitry for applying pacing pulses including antitachycardia atrial overdrive pacing to the atria with electrodes 37 and 39. Further, the pacer 55 may provide single chamber pacing in either the right ventricle 12 or right atrium 16, asynchronously or on demand, or dual chamber pacing. Such pacers and modalities are well known in the art. The pacer is coupled to the microprocessor over a line 56 to permit the microprocessor to configure the pacer 55 for any one of its pacing modalities including a continuous atrial pacing modality. The line 56 also provides a means by which the pacer 55 can provide the interrupt stage 70 with an input signal whenever the pacer 55 applies a pacing pulse to the heart. The interrupt stage 70 is thus able to determine when an atrial pacing pulse, for example, is applied to the heart by the pacer.

The following discussion assumes that the pacer has been placed into a continuous atrial pacing mode such as the AAI or AAIP mode. At predetermined times as described in U.S. Pat. No. 5,464,432 or based upon continuously monitored heart activity as described in U.S. Pat. No. 5,279,291, an atrial fibrillation detection is initiated by the sense amplifiers 50 and 54, the R wave detector 52, the atrial activity detector 60, the analog to digital converter 57, the multiplexer 45 and the DMA 59 being enabled. A data acquisition is first performed for a data acquisition period of, for example, eight seconds. During the eight second data acquisition period, the electrogram signals from sense amplifiers 50 and 54 are digitized by the analog to digital converter 57 into digital data and the digital data is caused to be stored in the memory 90 by the DMA 59 as previously described. Also during this time, each output of the R wave detector 52 causes an interrupt to the microprocessor 62. Each R wave interrupt is time stamped and the interrupt time stamps are stored in the memory 90 along with the digital data from DMA 59.

After the eight second data acquisition period is completed, the atrial fibrillation detector 64 is enabled and analyzes the stored electrogram data from the RACS channel. The atrial fibrillation detector 64 may determine if the atria 16 and 18 are in fibrillation in a manner known in the art as, for example, described in U.S. Pat. No. 5,486,199 which issued on Jan. 13, 1996 for "System and Method For Reducing False Positives In Atrial Fibrillation Detection," which patent is assigned to the assignee of the present invention and incorporated herein by reference. If the atria are in fibrillation and thus in need of cardioversion, the charge delivery control 74 causes the charger and storage capacitor circuit 76 to charge the storage capacitor within the circuit 76 to a selected peak voltage. After the capacitor is charged, another data acquisition is performed and the atrial fibrillation detector 64 confirms the presence of atrial fibrillation.

In accordance with a preferred embodiment of the present invention, after the confirmation of atrial fibrillation, the defibrillator 30 proceeds into a synchronization routine wherein the synchronization stage analyzes the atrial pacing pulse occurrences and intrinsic R waves. As previously mentioned, given the diminished atrial electrogram amplitudes during atrial fibrillation, the pacer 55 will most likely be performing fixed rate noninhibited atrial pacing while R waves are being produced in an unsynchronous and mixed manner. To locate a safe time to deliver therapy, the synchronization stage 66 includes the timer 68 which times time spans between immediately successive R waves and atrial pacing pulses. When such a time span exceeds a predetermined duration, such as 800 milliseconds, for example, the synchronization stage 66 causes the charge delivery and storage control 74 to discharge the storage capacitor of circuit 76 to apply the cardioverting energy to electrodes 44 and 46, and thus the atria. To determine the time spans between immediately successive atrial pacing pulses and R waves, the timer 68 may use the interrupts generated over line 56 from the pacer 55 and the R wave detections by R wave detector 52. Alternatively, the P wave detections could be performed by the microprocessor 62 with data received directly and on a real time basis from the DMA 59 over line 59C.

FIG. 2 illustrates the foregoing operation. The electrogram 110 includes detected R waves 112, 114, 116, 118, and 120 and atrial pacing pulses 122, 124, 126, and 128. The timer 68 times the time spans 134, 133, 132, 131 and 130 between each R wave and atrial pacing pulse. As illustrated, time span 130 is the first time span which exceeds the predetermined duration. As a result, the synchronization stage will cause the therapy to be delivered in time relation to atrial pacing pulse 126. Preferably, the therapy is applied synchronized to the atrial pacing pulse 126.

FIG. 3 illustrates another electrogram 140 having P waves 142, 144, 146, 148 and 150 and atrial pacing pulses 152, 154, 156, and 158. Here, time span 160 is the first time span of time spans 163, 162, 161 and 160 which exceeds the predetermined duration. As a result, the synchronization stage 66 will cause the therapy to be delivered in timed relation to R wave 148 and preferably, synchronized to R wave 148.

While particular embodiments of the present invention have been shown and described, modifications may be made. For example, it is contemplated that a separate pacemaker may be employed for pacing the atria. In this event, the presence of each atrial pacing pulse could be sensed by a sense amplifier of the defibrillator, such as the sense amplifier 51 of the defibrillator and such sensing be used to determine the time spans between successive R waves and atrial pacing pulses. It is therefore intended in the appended claims to cover all such changes and modifications which fall within the true spirit and scope of the invention.

What is claimed is:

1. An atrial cardioverter comprising:
   a pacemaker for applying atrial pacing pulses to an atrium of a heart;
   an atrial tachyarrhythmia detector for detecting an atrial tachyarrhythmia of the heart;
   an R wave detector for detecting R waves of the heart; and
   a cardioverting stage including a timer for timing time spans alternatingly between immediately successive R waves and subsequent atrial pacing pulses and between immediately successive atrial pacing pulses and subsequent R waves for applying cardioverting electrical energy to the atria of the heart responsive to such a time span exceeding a predetermined duration.

2. An atrial cardioverter as defined in claim 1 further including a synchronizing stage for causing the cardioverting electrical energy to be applied to the atria in timed relation to detected R wave.

3. An atrial cardioverter as defined in claim 1 further including a synchronizing stage for causing the application of the cardioverting electrical energy to be synchronized to a detected R wave.

4. An atrial cardioverter as defined in claim 1 further including a synchronizing stage for causing the application of the cardioverting electrical energy to be synchronized to an atrial pacing pulse.

5. An atrial cardioverter comprising:
   a pacemaker for applying atrial pacing pulses to an atrium of a heart;
   an atrial tachyarrhythmia detector for detecting an atrial tachyarrhythmia of the heart;
   an R wave detector for detecting R waves of the heart;
   cardioverting stage including a timer for timing time spans between immediately successive R waves and atrial pacing pulses for applying cardioverting electrical energy to the atria of the heart responsive to a time span exceeding a predetermined duration; and
   a synchronizing stage for causing the cardioverting electrical energy to be applied to the atria in timed relation to an atrial pacing pulse.

6. An atrial cardioverter for cardioverting atria of a heart in the presence of atrial pacing pulses being applied to the heart, comprising:
   means for determining when the atrial pacing pulses are applied to the heart;
   an atrial tachyarrhythmia detector for detecting an atrial tachyarrhythmia of the heart;
   an R wave detector for detecting R waves of the heart; and
   a cardioverting stage including a timer for timing time spans alternatingly between immediately successive R waves and subsequent atrial pacing pulses and between immediately successive atrial pacing pulses and subsequent R waves for applying cardioverting electrical energy to the atria of the heart responsive to such a time span exceeding a predetermined duration.

7. A method of cardioverting atria of a heart in the presence of applied pacing pulses to the atria of a heart, the method including the steps of:
   determining when the atrial pacing pulses are applied to the heart;
   detecting an atrial tachyarrhythmia of the heart;
   detecting R waves of the heart;
   timing time spans alternatingly between immediately successive R waves and subsequent atrial pacing pulses and between immediately successive atrial pacing pulses and subsequent R waves; and
   applying cardioverting electrical energy to the atria of the heart responsive to such a time span exceeding a predetermined duration.

8. A method for cardioverting atria of a heart, comprising the steps of:
   applying atrial pacing pulses to an atrium of a heart;
   detecting an atrial tachyarrhythmia of the heart;
   detecting R waves of the heart;
   timing time spans alternatingly between immediately successive R waves and subsequent atrial pacing pulses and between immediately successive atrial pacing pulses and subsequent R waves; and
   applying cardioverting electrical energy to the atria of the heart responsive to such a time span exceeding a predetermined duration.

9. The method of claim 8 wherein the step of applying cardioverting electrical energy to the atria of the heart includes the step of applying cardioverting electrical energy to the atria in timed relation to a detected R wave.

10. The method of claim 8 wherein the step of applying cardioverting electrical energy to the atria of the heart includes the step of applying cardioverting electrical energy to the atria synchronized to a detected R wave.

11. A method for cardioverting atria of a heart, comprising the steps of:
    applying atrial pacing pulses to an atrium of a heart;
    detecting an atrial tachyarrhythmia of the heart;
    detecting R waves of the heart;
    timing time spans between immediately successive R waves and atrial pacing pulses; and
    applying cardioverting electrical energy to the atria of the heart in timed relation to an atrial pacing pulse responsive to a time span exceeding a predetermined duration.

12. The method of claim 11 wherein the step of applying cardioverting electrical energy to the atria of the heart in timed relation to an atrial pacing pulse includes the step of applying cardioverting electrical energy to the atria synchronized to an atrial pacing pulse.

* * * * *